United States Patent
Yuan et al.

(10) Patent No.: US 10,543,154 B2
(45) Date of Patent: *Jan. 28, 2020

(54) ORAL CARE COMPOSITION

(71) Applicant: Colgate-Palmolive Company, New York, NY (US)

(72) Inventors: Shaotang Yuan, East Brusnwick, NJ (US); Guofeng Xu, Plainsboro, NJ (US); Robert Dicosimo, Chadds Ford, PA (US); Sharon Haynie, Philadelphia, PA (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/838,486

(22) Filed: Dec. 12, 2017

(65) Prior Publication Data

US 2018/0168972 A1 Jun. 21, 2018

Related U.S. Application Data

(60) Provisional application No. 62/436,805, filed on Dec. 20, 2016.

(51) Int. Cl.
| | |
|---|---|
| *A61K 8/37* | (2006.01) |
| *A61K 8/81* | (2006.01) |
| *A61Q 11/00* | (2006.01) |
| *A61K 8/90* | (2006.01) |

(52) U.S. Cl.
CPC .............. *A61K 8/37* (2013.01); *A61K 8/8182* (2013.01); *A61K 8/90* (2013.01); *A61Q 11/00* (2013.01); *A61K 2800/54* (2013.01)

(58) Field of Classification Search
None
See application file for complete search history.

(56) References Cited

U.S. PATENT DOCUMENTS

| | | |
|---|---|---|
| 3,480,557 A | 11/1969 | Shiraeff |
| 5,431,916 A | 7/1995 | White |
| 5,885,554 A | 3/1999 | Michael et al. |
| 6,004,582 A | 12/1999 | Faour et al. |
| 9,180,318 B2 * | 11/2015 | Deng ............ A61K 8/24 |
| 2003/0152528 A1 | 8/2003 | Singh et al. |
| 2003/0233549 A1 | 12/2003 | Singh et al. |
| 2004/0258723 A1 | 12/2004 | Singh et al. |
| 2005/0036956 A1 * | 2/2005 | Fei ............ A61K 8/22 424/53 |
| 2005/0281757 A1 | 12/2005 | Ibrahim et al. |
| 2006/0024245 A1 | 2/2006 | Gebresaelassie et al. |
| 2008/0014224 A1 | 1/2008 | Boyd et al. |
| 2009/0311198 A1 * | 12/2009 | Concar ........... A61K 8/22 424/50 |

FOREIGN PATENT DOCUMENTS

| | | |
|---|---|---|
| EP | 2056787 | 1/2014 |
| WO | WO 2000/009079 | 2/2000 |
| WO | 2014/102628 | 7/2014 |

OTHER PUBLICATIONS

Ash et al., 2014, "Specialty Chemicals Source Book," https://dow.com/webapps/include/GetDoc.aspx?filepath=productsafety/pdfs/noreg/233-00411.pdf.

International Search Report and Written Opinion of the International Searching Authority in International Application No. PCT/US2017/065683, dated Mar. 7, 2018.

\* cited by examiner

*Primary Examiner* — Celeste A Roney

(57) ABSTRACT

An oral care composition, including a non-aqueous dispersant and an amphiphilic copolymer structure-building agent.

14 Claims, No Drawings

ORAL CARE COMPOSITION

BACKGROUND

Generally, structure-building agents, also referred to as gelling agents, thickening agents, or thickeners are used in oral care composition to increase a viscosity of the oral care composition and to provide a structure to hold other ingredients of the oral care composition in a homogenous state or in a chemically and/or physically stable environment.

Structure-building agents may be hydrophilic or hydrophobic. Hydrophilic gelling agents, such as polyvinylpyrrolidone (PVP), Carbopol, etc., are used to provide a homogenous structure for aqueous products, while hydrophobic gelling agents, such as plastic gels, are used for products containing large amount of a hydrophobic oil, e.g., mineral oil. However, conventional structure-building agents, such as PVP, Carbopol, plastic gels, etc., are not able to provide a fully homogenous structure to oral care compositions when the oral care composition includes significant amounts of non-aqueous liquids used as dispersants.

Accordingly, there is a desire for structure-building agents that can provide a stable and homogeneous structure to oral care compositions that include non-aqueous liquids.

BRIEF SUMMARY

This section is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition, including from about 0.01% to about 99% of a non-aqueous dispersant, based on the total weight of the oral care composition, and from about 0.01% to about 60% of amphiphilic copolymer structure-building agent, based on the total weight of the oral care composition.

In another embodiment, the non-aqueous dispersant includes a non-aqueous liquid selected from the group consisting of glycerin monoacetate, triacetin, diethylene glycol diacetate, ethylene glycol diacetate, and propylene glycol diacetate (PGDA).

In another embodiment, the non-aqueous dispersant includes a liquid poloxamer or a paste poloxamer.

In another embodiment, the amphiphilic copolymer structure-building agent includes a vinyl pyrrolidone copolymers.

In another embodiment, the amphiphilic copolymer structure-building agent includes at least one of PVP-VA, PVP-VB, and PVP-VP.

In another embodiment, the non-aqueous liquid includes triacetin.

In another embodiment, the non-aqueous liquid includes PGDA.

In another embodiment, a viscosity of the oral care composition is from about 10,000 to about 500,000 cPs.

In another embodiment, the oral care composition further includes at least one orally acceptable ingredient from the group consisting of: a whitening agent, a surfactant, an antioxidant, a flavoring, a sweetener, a pH modifiers, an abrasive, an anticalculus agent, a source of fluoride ions, a stannous ion source, a colorant, a dye, and a pigment.

In another embodiment, the oral care composition is a dentifrice.

In another embodiment, the non-aqueous dispersant includes a low water content dispersant.

In another embodiment, the oral care composition includes from about 20 weight % to about 80 weight % of a non-aqueous dispersant, and from about 1 weight % to about 30 weight % of amphiphilic copolymer structure-building agent, wherein the non-aqueous dispersant includes at least one of glycerin monoacetate, triacetin, diethylene glycol diacetate, ethylene glycol diacetate, and propylene glycol diacetate (PGDA), and wherein the amphiphilic copolymer structure-building agent includes a vinyl pyrrolidone copolymers.

In another embodiment, the oral care composition includes an equal or greater amount of non-aqueous dispersant to amphiphilic copolymer structure-building agent, such that a mass ratio of the non-aqueous dispersant to the amphiphilic copolymer structure-building agent is 50:50 or greater.

In another embodiment, a mass ratio of the non-aqueous dispersant to the amphiphilic copolymer structure-building agent is from about 90 to 50 non-aqueous dispersant to about 10 to 50 amphiphilic copolymer structure-building agent.

The foregoing and/or other aspects and utilities embodied in the present disclosure may be achieved by providing an oral care composition includes from about 0.01% to about 99% of a non-aqueous liquid, based on the total weight of the oral care composition, and from about 0.01% to about 60% of amphiphilic copolymer structure-building agent, based on the total weight of the oral care composition, wherein the non-aqueous liquid includes at least one of glycerin monoacetate, triacetin, diethylene glycol diacetate, ethylene glycol diacetate, and propylene glycol diacetate (PGDA), wherein the amphiphilic copolymer structure-building agent includes a vinyl pyrrolidone copolymers, and wherein the oral care composition includes an equal or greater amount of non-aqueous liquid to amphiphilic copolymer structure-building agent, such that a mass ratio of the non-aqueous liquid to the amphiphilic copolymer structure-building agent is 50:50 or greater.

The foregoing and/or other aspects and utilities embodied in the present disclosure may be achieved by providing an oral care composition substantially as hereinbefore described, with reference to the examples and excluding, if any, comparative examples.

DETAILED DESCRIPTION

The embodiments are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the embodiments.

Throughout the specification and claims, the following terms take the meanings explicitly associated herein, unless the context clearly dictates otherwise. The phrases "in some embodiments" and "in an embodiment" as used herein do not necessarily refer to the same embodiment(s), though they may. Furthermore, the phrases "in another embodiment" and "in some other embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/ B/B/C, A/B/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, component, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate valves and ranges, whether "about" is used in conjunction therewith.

With regard to procedures, methods, techniques, and workflows that are in accordance with some embodiments, some operations in the procedures, methods, techniques, and workflows disclosed herein may be combined and/or the order of some operations may be changed.

According to one embodiment, an oral care composition may include a structure-building agent and a non-aqueous dispersant. In some embodiments, the non-aqueous dispersant includes a non-aqueous liquid. As used herein, the term "non-aqueous" or "non-aqueous liquid" refers to a substance, or mixture of substances, that has a moisture content of 5% or less by weight.

In one embodiment, the dispersant is non-aqueous, but the dispersant is sufficiently hydrophilic to react in an aqueous environment.

In some embodiment, the partition coefficient value (log P) may be used to determine the amphiphilic characteristics of an ingredient. For example, the partition coefficient value may be used as a measure of lipophilicity. Large positive log P values indicate a lipophilic or hydrophobic nature, whereas, large negative log P value indicate a lipophobic or hydrophilic nature. In some embodiments, the non-aqueous liquid has a log P value of about −2 to about +2.

In one embodiment, the non-aqueous dispersant is a poloxamer. In some embodiments, the non-aqueous dispersant is a liquid or paste like poloxamer, with average molecular weight less than 7000 Dalton. For example, the dispersant may include one or more of Pluronic® L35, Pluronic® L43, Pluronic® L64, Pluronic® L10, Pluronic® L44, Pluronic® L62, Pluronic® 10R5, Pluronic® 17R4, Pluronic® L25R4, Pluronic® P84, Pluronic® P65, Pluronic® P104, and Pluronic® P105. Pluronic® brand dispersants are commercially available from BASF, Florham Park, N.J.

In one embodiment, the oral care composition includes from about 0.01% to about 99%/non-aqueous dispersant based on the total weight of the oral care composition. In another embodiment, the oral care composition includes from about 1 weight % to about 70 weight % non-aqueous dispersant. In yet another embodiment, the oral care composition includes from about 5 weight % to about 50 weight % non-aqueous dispersant. For example, in one embodiment, the oral care composition includes from about 0.01 weight % to about 99 weight % L35, from about 1 weight % to about 70 weight % L35, or from about 5 weight % to about 50 weight % L35.

In other embodiments, the oral care composition includes one or more non-aqueous liquids as non-aqueous dispersants or liquid carriers. In some embodiments, the non-aqueous liquid is a hydrophobic non-aqueous liquid.

In some embodiments, the structure-building agent is combined with one or more non-aqueous liquids to create a gel. For example, in some embodiments, the oral care composition may include a gel formed from combining a structure-building agent with one or more of glycerin monoacetate, triacetin, diethylene glycol diacetate, ethylene glycol diacetate, and propylene glycol diacetate (PGDA) as a non-aqueous liquid. Triacetin is commercially available as Glyceryl triacetate, from Spectrum Chemical MFG Corp. Propylene Glycol Diacetin (PGDA) is commercially available from Sigma-Aldrich Corp.

Triacetin

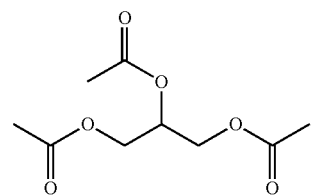

Propylene Glycol Diacetate (PGDA)

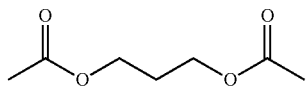

PVP-VA

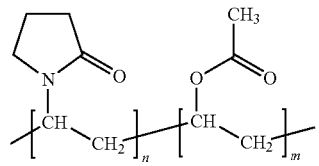

In one embodiment, the oral care composition includes from about 0.01% to about 99% non-aqueous liquid(s) based on a total weight of the oral care composition. In another embodiment, the oral care composition includes from about 1 weight % to about 70 weight % non-aqueous liquid(s). In yet another embodiment, the oral care composition includes from about 5 weight % to about 50 weight % non-aqueous liquid(s). For example, in one embodiment, the oral care composition includes from about 0.01 weight % to about 99 weight % triacetin, from about 1 weight % to about 70 weight % triacetin, or from about 5 weight % to about 50 weight % triacetin. In one example, the oral care composition includes about 26 weight % triacetin based on the total weight of the oral care composition. In other embodiments, the oral care composition includes from about 0.01 weight % to about 99 weight % PGDA, from about 1 weight % to about 70 weight % PGDA, or from about 5 weight % to about 50 weight % PGDA.

Oral care compositions may comprise a structure-building agent capable of holding other ingredients of the oral care composition in a homogenous state or in a chemically and/or physically stable environment. However, conventional structure-building agents, such as polyvinylpyrrolidone (PVP), Carbopol, plastic gels, etc., are not able to provide a homogenous structure to oral care compositions when the oral care composition includes significant amounts of non-aqueous liquids. Instead, when the oral care composition containing conventional structure-building agents is mixed into a gel with non-aqueous liquids, physical separation of the gel normally occurs within a few hours after the gel is made.

Accordingly, in some embodiments, the oral care composition may also include one or more amphiphilic copolymer structure-building agents capable of creating a stable and homogenous gel with non-aqueous dispersants or non-aqueous liquids in the oral care composition.

As used herein, an "amphiphilic copolymer" refers to a copolymer of two or more monomers, of which at least one is hydrophilic in nature, such as vinyl pyrrolidone, and at least one is hydrophobic in nature, such as vinyl acetate. In one embodiment, amphiphilic copolymers are able to interact with both hydrophilic and hydrophobic liquid dispersants to help build structures with these liquids or their mixtures to produce a gel. For example, the oral care composition may include amphiphilic copolymers of vinyl pyrrolidone and esters of vinyl alcohol, such as PVP-VA (polyvinyl pyrrolidone co vinyl acetate), PVP-VB (polyvinyl pyrrolidone co vinyl butyrate) and PVP-VP (polyvinyl pyrrolidone co vinyl propionate).

In one embodiment, the structure-building agent may include a polyvinylpyrrolidone-vinyl acetate copolymer (PVP-VA) (e.g., commercially available as Plasdone S-630 from Ashland Inc.). The molecular structure of PVP-VA may be represented as follows:

In other embodiments, the structure-building agent may also include polyvinyl pyrrolidone-co-polyvinyl butyrate copolymer (PVP-VB), polyvinyl pyrrolidone-co-polyvinyl propionate copolymer, or mixtures thereof.

In one embodiment, the oral care composition includes from about 0.01% to about 99% non-aqueous liquid and from about 0.01% to about 60% structure-building agent, based on the total weight of the oral care composition. In another embodiment, the oral care composition includes from about 1 weight % to about 70 weight % non-aqueous liquid and from about 1 weight % to about 50 weight % structure-building agent. In yet another embodiment, the oral care composition includes from about 5 weight % to about 50 weight % non-aqueous liquid and from about 5 weight % to about 40 weight % structure-building agent. For example, in one embodiment, the oral care composition includes from about 10 weight % to about 95 weight % triacetin and from about 0.1 weight % to about 40 weight % PVP-VA, or from about 20 weight % to about 80 weight % triacetin and from about 1 weight % to about 30 weight % PVP-VA.

In other embodiments, the amount of non-aqueous liquid and structure-building agent may be defined as a ratio. For example, in one embodiments, the oral care composition includes a mass ratio of 90:10 of the non-aqueous liquids to structure-building agent. In other embodiments, the non-aqueous liquid to structure-building agent mass ratio is 70:30 or 50:50. For example, in some embodiments, the oral care composition may be formed of a gel having a 70:30 triacetin:PVP-VA mass ratio. In some embodiments, the gel may have a 60:40 triacetin:PVP-VA mass ratio, or a 50:50 triacetin:PVP-VA mass ratio. In some embodiments, the gel has a 2.3 to 3.3 to 1 triacetin:PVP-VA mass ratio. In other embodiments, the oral care composition may be formed of a gel having a 70:30 PGDA:PVP-VA mass ratio, or a 60:40 PGDA:PVP-VA mass ratio. In some embodiments, the gel has a 1.8 to 1.9 to 1 PGDA:PVP-VA mass ratio.

Generally, viscosity is an important parameter for oral care compositions, such as toothpastes or whitening gels. For example, when the viscosity of an oral care composition is too low, it may become too runny and physical phase separation may take place. In some cases, this will not only affect the aesthetics of the oral care composition but also the homogeneity of the ingredients in the oral care composition. On the other hand, if the viscosity of the oral care compositions is too high, the oral care composition will be difficult to manufacture and package. In addition, oral care compositions with high viscosity are very difficult for users to evacuate from commonly used packages, such as tubes or syringes. In some embodiments, the gel formed of the structural building agent and the non-aqueous liquids helps determine the overall viscosity of the oral care composition. Accordingly, it's important to select ingredients for oral care compositions that achieve a desirable range of viscosity to ensure product manufacturability, stability, and quality, as well as consumer acceptance.

In some embodiments, the viscosity of the oral care composition is from about 10,000 centipoise (cPs) to about 500,000 cPs at 25° C. In other embodiments, the viscosity of the oral care composition is from about 50,000 cPs to about 400,000 cPs at 25° C. In one embodiment, the viscosity of the oral care composition is from about 125,000 cPs to about 300,000 cPs at 25° C.

According to some embodiments, the structure-building agent is capable of creating a stable and homogenous gel with the non-aqueous liquids in an oral care composition. For example, a homogenous and transparent or semi-transparent gel can be created from combining an amphiphilic copolymer structure-building agent, such as PVP-VA, with a non-aqueous liquid dispersant, such as triacetin, diacetin, propylene glycol diacetin, etc.

In some embodiments, the oral care composition may include additional ingredients common to oral care compositions, such as additional dispersants, whitening agents, flavoring agents, tartar control agents, surfactants, sweeteners, humectants, colorants, dyes, and pigments.

All ingredients used in the compositions described herein should be orally acceptable. "Orally acceptable" means an ingredient which is present in the composition as described in an amount and form which does not render the composition unsafe, unpalatable, or otherwise unsuitable for use in the oral cavity.

In some embodiments, the oral care composition includes a combination of non-aqueous or suitable low water content dispersants in addition to a poloxamer and/or a non-aqueous liquid. For example, in some embodiments, the oral care composition may include one or more of polyethylene glycols, such as PEG400 and PEG600, or polyethylene/polypropylene glycol copolymers, such as PEG/PPG 38/8 and PEG/PPG-116/66.

As described above, the oral care composition includes one or more whitening agent. As used herein, a "whitening agent" is a material which effects whitening of a tooth surface to which it is applied. For example, in some embodiments, the whitening agent is an oxidizing agent. In its broadest sense, "oxidizing agent" is intended to include those compounds which can accept an electron from another molecule in the environment of the oral cavity without having a deleterious or unacceptably harmful effect on the oral cavity in normal and accepted use.

In some embodiments, the whitening agent may include peroxides and hydroperoxides, such as hydrogen peroxide, peroxides of alkali and alkaline earth metals, organic peroxy compounds, peroxy acids, salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include urea peroxide, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as percarbonate, perphosphate, perborate and persilicate salts of alkali and alkaline earth metals such as lithium, potassium, sodium, magnesium, calcium and barium, and mixtures thereof. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite.

In some embodiments, the oral care composition includes from about 0.01% to about 50% whitening agent based on a total weight of the oral care composition. In other embodiments, the oral care composition includes from about 0.05 weight % to about 40 weight % whitening agent. In one embodiment, the oral care composition includes about 0.1 weight % whitening agent based on a total weight of the oral care composition.

In one embodiment, the oral care composition includes one or more surfactants. In some embodiments, the surfactants enhance stability of the composition, help clean the oral cavity surfaces through detergency, and provide foam upon agitation, e.g., during brushing with an oral care composition of the disclosure. Surfactants or surface active agents generally achieve increased whitening action by thoroughly dispersing the whitening agent throughout the oral cavity. In various embodiments, suitable surface active agents may function as a surface active agent, emulsifier, and/or foam modulator.

Any orally acceptable surfactant, most of which are anionic, nonionic, cationic, or amphoteric, can be used. A combination of surfactants may also be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium cocoyl monoglyceride sulfonate, sodium lauryl sarcosinate, sodium lauryl isoethionate, sodium laureth carboxylate, and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

In some embodiments, the oral care composition includes from about 0.01% to about 20.0% surfactant based on a total weight of the oral care composition. In other embodiments, the oral care composition includes from about 1.0 weight % to about 10.0 weight % surfactant. In one embodiment, the oral care composition includes about 2 weight % surfactant based on a total weight of the oral care composition. For example, the oral care composition may include about 2 weight % sodium lauryl sulfate.

In other embodiments, the oral care composition may include additional structure-building agents. For example, the oral care composition may include a cross-linked polymer, such as cross-linked polyvinylpyrrolidone ("PVP") in addition to the amphiphilic copolymer structure-building agents, such as PVP-VA. In one embodiment, the structure-building agent includes cross-linked polymers capable of interacting with the dispersants. For example, in some embodiments, cross-linked PVP swells in the presence of poloxamers by absorbing them into its cross-linked polymer network. Such interaction helps to prevent the solid (cross-linked PVP) from phase separating from the liquid dispersant in the oral care composition.

According to some embodiments, suitable structure-building agent polymers and copolymers include N-vinyl lactam based polymers and copolymers. The monomers for preparing a vinyl lactam-based polymer or co-polymer of the present application includes any monomer having 3 to 8 atoms in a heterocyclic ring, comprising a carbonyl carbon atom and a heteroatom (such as N, S, O) in its vinyl moiety. Suitable monomers include but not limited to N-vinyl-2-pyrrolidone, N-vinyl-2-piperidone, N-vinyl-3-methyl-pyrrolidinone, N-vinyl-3-methyl-piperidone, N-vinyl-3-methyl-caprolactam, N-vinyl-4-methyl-pyrrolidinone, N-vinyl-4-methyl-2-pyrrolidone, N-vinyl-4-methyl-piperidone, N-vinyl-4-methyl-caprolactam, N-vinyl-5-methyl-pyrrolidinone. N-vinyl-5-ethyl-2-pyrrolidone, N-vinyl-4-methyl-piperidone, N-vinyl-3-ethyl-pyrrolidinone, N-vinyl-4,5-dimethyl-pyrrolidinone, N-vinyl-5,5-dimethyl-pyrrolidinone, N-vinyl-3,3,5-trimethyl-pyrrolidinone, N-vinyl-5-methyl-5-ethyl-pyrrolidinone, N-vinyl-3,4,5-trimethyl-3-ethyl-pyrrolidinone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-2-caprolactam, N-vinyl-7-methyl-caprolactam, N-vinyl-7-ethyl-caprolactam, N-vinyl-3,5-dimethyl-caprolactam, N-vinyl-4,6-dimethyl-caprolactam, N-vinyl-3,5,7-trimethyl-caprolactam, N-vinyl-2-valerolactam, N-vinyl-hexahydro-2-azepinone, N-vinyl-octahydro-2-azocinone. N-vinyl octahydro-2-azoninone, and N-vinyl decahydro-2-azecinone.

The polymer may be a cross-linked polyvinylpyrrolidone, also known as poly-N-vinyl-poly-2-pyrrolidone, and commonly abbreviated to cross-linked "PVP." PVP generally refers to a polymer containing vinylpyrrolidone (also referred to as N-vinylpyrrolidone, N-vinyl-2-pyrrolidione and N-vinyl-2-pyrrolidinone) as a monomeric unit. The monomeric unit may include a polar imide group, four non-polar methylene groups, and a non-polar methane group. Cross linked PVP includes those commercially available as KOLLIDON® and LUVICROSS®, marketed by BASF, Mount Olive, N.J., USA; and POLYPLASDONE® INF-10, marketed by, Ashland, Covington, Ky., USA.

In some embodiments, the oral care composition may include additional thickening agents. Any orally acceptable thickening agent can be used, including without limitation carbomers, also known as carboxyvinyl polymers, carrageenans, also known as Irish moss and more particularly carrageenan (iota-carrageenan), high molecular weight polyethylene glycols (such as CARBOWAX™, available from The Dow Chemical Company), cellulosic polymers such as hydroxyethylcellulose, carboxymethylcellulose ("CMC") and salts thereof, e.g., CMC sodium, natural gums such as karaya, xanthan, gum arabic and tragacanth, colloidal magnesium aluminum silicate, and colloidal or fumed silica and mixtures of the same. The thickening agent may be a combination of one or more orally acceptable thickening agents.

In some embodiments, the oral care composition includes from about 0.01% to about 30% thickening agent based on a total weight of the oral care composition. In other embodiments, the oral care composition includes from about 0.1 weight % to about 20 weight % thickening agent. In yet another embodiment, the oral care composition includes from about 0.5 weight % to about 10 weight % thickening agent based on a total weight of the oral care composition. For example, the oral care composition may include about 3 weight % fumed silica.

In some embodiments, the oral care composition includes an antioxidant. Acceptable antioxidants include BHA, BHT, vitamin A, carotenoids, vitamin E, flavonoids, polyphenols, ascorbic acid, herbal antioxidants, chlorophyll, melatonin and mixtures thereof. In some embodiments, the oral care composition includes from about 0.001% to about 1% antioxidants based on a total weight of the oral care composition. In one embodiment, the oral care composition includes about 0.03 weight % antioxidant by weight.

According to one embodiment, the oral care composition includes one or more flavoring agent. Useful flavoring agents include any material or mixture of materials operable to enhance the taste of the oral care composition. Any orally acceptable natural or synthetic flavoring agent can be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methylsalicylate), peppermint oil, clove oil, bay oil, anise oil, *eucalyptus* oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, *eucalyptus* oil, eucalyptol, anethole, eugenol, *cassia*, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA) and mixtures thereof.

In some embodiments, the oral care composition includes from about 0.01% to about 5% flavoring agents based on a total weight of the oral care composition. In another embodiment, the oral care composition includes from about 0.05 weight % to about 3 weight % flavoring agents. In yet another embodiment, the oral care composition includes from about 0.1 weight % to about 3 weight %, from about 0.2 weight % to about 2.5 weight %, or about 1.5 weight % flavoring agents based on a total weight of the oral care composition. For example, the oral care composition may include about 1.5 weight % of dental cream flavor.

In some embodiments, the oral care composition may also include one or more sweeteners. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Some embodiments may include one or more sweeteners. In some embodiments, the oral care composition includes from about 0.005% to about 5% sweeteners based on a total weight of the oral care composition. In other embodiments, the oral care composition includes from about 0.01% to about 1% sweeteners. For example, the oral care composition may include about 0.5 weight % sodium saccharin and about 0.04 weight % sucralose.

In some embodiments, the oral care composition may also include one or more pH modifying agents. PH modifying agents among those useful herein include acidifying agents to lower pH, basifying agents to raise pH and buffering agents to control pH within a desired range. For example, one or more compounds selected from acidifying, basifying and buffering agents can be included to provide a pH of 2 to 10, or in various embodiments from about 2 to about 8, from about 3 to about 9, from about 4 to about 8, from about 5 to about 7, from about 6 to about 10, and from about 7 to about 9. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range. In some embodiments, the oral care composition includes from about 0.01% to about 10% pH modifier agents based on a total weight of the oral care composition. For example, the oral care composition may include about 0.9 weight % sodium acid pyrophosphate (SAPP) and about 2 weight % tetrasodium pyrophosphate (TSPP) as a pH modifier.

In some embodiments, the oral care composition may include colorants. Colorants, such as dyes or pigments, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

The oral compositions of the present disclosure may also include one or more other active ingredients, which are operable for the prevention or treatment of a condition or disorder of hard or soft tissue of the oral cavity, the prevention or treatment of a physiological disorder or condition, or to provide a cosmetic benefit.

Some embodiments of the present disclosure include a dental abrasive or combination of dental abrasive agents. As used herein, the term "abrasive" or "abrasive agent" also includes materials commonly referred to as "polishing agents." Any orally acceptable abrasive can be used, but typically, type, fineness (particle size) and amount of abrasive should be selected so that tooth enamel is not excessively abraded in normal use of the composition. Suitable abrasives include without limitation silica (in the form of silica gel, hydrated silica or precipitated silica), alumina, insoluble phosphates, calcium carbonate, resinous abrasives such as urea-formaldehyde condensation products and the like.

Among insoluble phosphates useful as abrasives are orthophosphates, polymetaphosphates and pyrophosphates. Illustrative examples are dicalcium orthophosphate dihydrate, calcium pyrophosphate, n-calcium pyrophosphate, tricalcium phosphate, calcium polymetaphosphate and insoluble sodium polymetaphosphate.

Average particle size of an abrasive, if present, is generally from about 0.1 to 100 about μm. For example, in one embodiment, the particle size is from about 1 to about 80 μm or from about 5 to about 60 μm. In some embodiments, one or more abrasives are present in an amount of from about 0.01% to about 70% by weight, based on the total weight of the oral care composition. In other embodiments, the oral care composition includes from about 0.1 weight % to about 60 weight % abrasives. In some embodiments, the abrasive is calcium pyrophosphate. In some embodiments, the oral care composition includes from 0.01 weight % to about 70 weight % calcium pyrophosphate based on a total weight of the oral care composition. In another embodiment, the oral care composition includes about 20 weight % calcium pyrophosphate.

In various embodiments of the present disclosure, the oral care composition includes an anticalculus agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments, the anticalculus agent is present in an amount of from about 0.01% to about 30% weight based on the total weight of the oral care composition. In some embodiments, the oral care composition includes a mixture of anticalculus agents. In some embodiments, tetrasodium pyrophosphate (TSPP) and sodium tripolyphosphate (STPP) are used as the anticalculus agents. In some embodiments, the anticalculus agent includes from 0.1% to 10 weight % TSPP, or about 2 weight % TSPP.

Another component of the present compositions may be a synthetic anionic polymeric polycarboxylate, which acts as a stabilizer for the polyphosphate anti-tartar agent and which may help to block access of painful or pain-causing materials, such as sugars, to the tooth nerves.

In some embodiments, the oral care composition optionally includes a source of fluoride ions. In some embodiments, the source of fluoride ions is selected from: fluoride, monofluorophosphate (MFP), and fluorosilicate salts. In some embodiments, one or more fluoride ion-releasing compounds are optionally present in an amount providing a total of 100 to 20,000 ppm, 200 to 5,000 ppm, or 500 to 2,500 ppm, fluoride ions. If present, in some embodiments, the amount of fluoride source in the oral care composition ranges from about 0.01% to about 10% by weight, based on the total weight of the oral care composition, typically about 1.1 weight %. For example, in one embodiment, the oral care composition may include about 0.76 weight % MFP.

The compositions also may include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. In some embodiments, one or more stannous ion sources are included in the oral care composition. For example, the oral care composition may include from about 0.01% to about 10% stannous ion source by weight, based on the total weight of the oral care composition. In one embodiment, the oral care composition includes from about 0.1 weight % to about 7 weight % stannous ion source or from about 0.2 weight % to about 5 weight % stannous ion source.

EXAMPLES

Aspects of the present disclosure may be further understood by referring to the following examples. The examples are illustrative, and are not intended to be limiting embodiments thereof. Example 1 illustrates a method of making a gel by combining a structure-building agent with a non-aqueous liquid. Tables 1 and 2 illustrate the gelling results for the gels created under Example 1.

Example 1

A gel was created by mixing pre-measured amounts of PVP-VA (Plasdone S-630, Ashland Inc.) with pre-measured amounts of triacetin (Glyceryl triacetate, Spectrum Chemical MFG Corp.) or PGDA (Sigma-Aldrich Corp). Various mass ratios of the PVP-VA and the triacetin or PDGA were mixed on a stir plate at about 55° C. for about 5-15 minutes.

Table 1 illustrates 12 samples that were prepared with Triacetin:PVP-VA mass ratios ranging from 99:1 to 1.5:1.

TABLE 1

| Sample No. | Triacetin (g) | PVP-VA (g) | % PVP-VA | Triacetin:PVP-VA mass ratio | Results |
|---|---|---|---|---|---|
| 1 | 9.9 | 0.1 | 1% | 99:1 | Clear homogeneous solution, but viscosity increases as PVP-VA amount increases. |
| 2 | 9.8 | 0.2 | 2% | 49:1 | |
| 3 | 9.7 | 0.3 | 3% | 32.3:1 | |
| 4 | 9.6 | 0.4 | 4% | 24:1 | |
| 5 | 9.5 | 0.5 | 5% | 19:1 | |
| 6 | 9.4 | 0.6 | 6% | 15.7:1 | |
| 7 | 9.4 | 1.2 | 11.32% | 7.8:1 | Solution is thicker |
| 8 | 9.9 | 2.0 | 16.8% | 4.95:1 | Solution is thicker, gel is forming |
| 9 | 9.8 | 3.0 | 23.44% | 3.3:1 | Gel formed. |
| 10 | 7.0 | 3.0 | 30% | 2.3:1 | Thick honey-like gel formed. |
| 11 | 6.5 | 3.5 | 35% | 1.86:1 | Thicker gel formed |
| 12 | 6.0 | 4.0 | 40% | 1.5:1 | Very thick and stringy gel formed. |

Table 2 shows 6 samples that were prepared with PGDA:PVP-VA mass ratios ranging from 19:1 to 1:1.

TABLE 2

| Sample No. | PGDA (g) | PVP-VA (g) | % PVP-VA | PGDA:PVP-VA mass ratio | Results |
|---|---|---|---|---|---|
| 1 | 9.5 | 0.5 | 5% | 19:1 | Homogenous solution formed |
| 2 | 9.0 | 1.0 | 10% | 9:1 | Homogenous solution formed |
| 3 | 8.0 | 2.0 | 20% | 4:1 | Solution thickening |
| 4 | 7.0 | 3.0 | 30% | 2.3:1 | Gel formed |
| 5 | 6.5 | 3.5 | 35% | 1.86:1 | Gel become thicker |
| 6 | 5.0 | 5.0 | 50% | 1:1 | Thick gel |

As illustrated in Table 1, mixtures containing triacetin become thicker as the amount of PVP-VA increases. A gel structure starts forming when the mass ratio of triacetin:PVP-VA reaches about 5:1. A thick honey-like gel forms as the mass ratio of triacetin:PVP-VA reaches 2.3:1. And an even thicker homogenous gel forms at a mass ratio of 1.5:1.

Table 2 illustrate the gelling results of PVP-VA on a slightly more lipophilic non-aqueous liquid, PGDA, which has a molecular structure similar to that of triacetin. As illustrated in Table 2, mixtures containing PGDA become thicker as the amount of PVP-VA increases, and a fine gel structure is formed as the mass ratio of PGDA/PVP-VA reaches 1:1.

As illustrated in Tables 1 and 2, homogenous and transparent or semi-transparent gels can be created by mixing amphiphilic copolymer structure-building agents, such as PVP-VA, with non-aqueous liquids, such as triacetin or PGDA. Transparent or semi-transparent gels are formed even when the amount of the non-aqueous liquids is greater than 50%.

In some embodiments, the present disclosure provides methods to apply the oral composition to an oral surface in a human or animal subject. The method may include contacting a tooth surface with an oral care composition according to embodiments of the present disclosure. As used herein "animal subject" includes non-human mammals, such as canines, felines and horses. In one embodiment, the oral care composition is contacted with an oral surface of the mammalian subject to thereby treat or whiten teeth in a highly efficacious manner.

In various embodiments, the oral care composition prepared in accordance with the present disclosure may be applied regularly to an oral surface, for example on a daily basis, at least one time daily for multiple days, or alternately every second or third day. In some embodiments, the oral care composition is applied to the oral surfaces from 1 to 3 times daily, for at least 2 weeks up to 8 weeks, from four months to three years, or more up to a lifetime.

In some embodiments, the oral care composition may be embodied as a gel and may be applied directly to the teeth using a delivery device, such as a pen, a liquid stick having an applicator, such as a felt tip, brush, roller ball, or non-woven pad. In some embodiments, the oral care composition is activated once exposed to the aqueous environment of the oral cavity or when exposed directly to water or saliva. In some embodiments, the oral care composition of the present disclosure is maintained on the surface of the tooth for a plurality of minutes.

In some embodiments, the oral care composition is activated and maintained on the surface of a tooth for from about 1 minute to about 8 hours. In some embodiments, the oral care composition is activated and maintained on the surface of a tooth for from about 5 minutes to about 4 hours. In some embodiments, the oral care composition is activated and maintained on the surface of a tooth for from about 10 minutes to about 120 minutes. In some embodiments, the oral care composition is activated and maintained on the surface of a tooth for from about 15 minutes to about 60 minutes. In some embodiments, the oral care composition is activated and maintained on the surface of a tooth for from about 20 minutes to about 45 minutes.

The present disclosure has been described with reference to exemplary embodiments. Although a limited number of embodiments have been shown and described, it will be appreciated by those skilled in the art that changes may be made in these embodiments without departing from the principles and spirit of preceding detailed description. It is intended that the present disclosure be construed as including all such modifications and alterations insofar as they come within the scope of the appended claims or the equivalents thereof.

What is claimed is:

1. An oral care composition, comprising:
   from about 60% to about 99% of a non-aqueous liquid, based on the total weight of the oral care composition, and
   from about 20% to about 50% of amphiphilic copolymer structure-building agent, based on the total weight of the oral care composition;
   wherein the mass ratio of non-aqueous liquid to amphiphilic copolymer structure-building agent is from 3.3:1 to 1:1.

2. The oral care composition of claim 1, wherein the non-aqueous liquid comprises a non-aqueous liquid selected from the group consisting of glycerin monoacetate, triacetin, diethylene glycol diacetate, ethylene glycol diacetate, and propylene glycol diacetate (PGDA).

3. The oral care composition of claim 1, wherein the non-aqueous liquid comprises a liquid poloxamer or a paste poloxamer.

4. The oral care composition of claim 1, wherein the amphiphilic copolymer structure-building agent comprises a copolymer comprising a vinyl pyrrolidone monomer.

5. The oral care composition of claim 4, wherein the amphiphilic copolymer structure-building agent comprises at least one of PVP-VA, PVP-VB, and PVP-VP.

6. The oral care composition of claim 2, wherein the non-aqueous liquid comprises triacetin.

7. The oral care composition of claim 2, wherein the non-aqueous liquid comprises PGDA.

8. The oral care composition of claim 1, wherein a viscosity of the oral care composition is from about 10,000 to about 500,000 cPs.

9. The oral care composition of claim 1, further comprising at least one orally acceptable ingredient from the group consisting of: a whitening agent, a surfactant, an antioxidant, a flavoring agent, a sweetener, a pH, modifier, an abrasive, an anticalculus agent, a source of fluoride ions, a stannous ion source, a colorant, a dye, and a pigment.

10. The oral care composition of claim 1, wherein the oral care composition is a dentifrice.

11. The oral care composition of claim 1, wherein the non-aqueous liquid comprises a low water content dispersant.

12. An oral care composition, comprising:
    from about 50% to about 95% of a non-aqueous liquid, based on the total weight of the oral care composition, and
    from about 30% to about 50% of amphiphilic copolymer structure-building agent, based on the total weight of the oral care composition,
    wherein the non-aqueous liquid is selected from: triacetin; and propylene glycol diacetate (PGDA);
    wherein the amphiphilic copolymer structure-building agent comprises a copolymer of polyvinyl pyrrolidone and vinyl acetate; and
    wherein the mass ratio of non-aqueous liquid to amphiphilic copolymer structure-building agent is from 2.3:1 to 1:1.

13. The oral care composition of claim 1, wherein the mass ratio of non-aqueous liquid to amphiphilic copolymer structure-building agent is from about 2.3:1 to about 1:1.

14. The oral care composition of claim 1, further comprising a peroxide whitening agent.

* * * * *

UNITED STATES PATENT AND TRADEMARK OFFICE
CERTIFICATE OF CORRECTION

PATENT NO. : 10,543,154 B2  
APPLICATION NO. : 15/838486  
DATED : January 28, 2020  
INVENTOR(S) : Shaotang Yuan et al.

Page 1 of 1

It is certified that error appears in the above-identified patent and that said Letters Patent is hereby corrected as shown below:

On the Title Page

In item "(72) Inventors", Line 1, delete "Brusnwick," and insert -- Brunswick --, therefor.

In the Specification

In Column 4, Line 30, delete "99%/non-aqueous" and insert -- 99% non-aqueous --, therefor.

Signed and Sealed this
Twenty-sixth Day of May, 2020

Andrei Iancu
*Director of the United States Patent and Trademark Office*